United States Patent
Eremin et al.

(10) Patent No.: US 6,169,601 B1
(45) Date of Patent: Jan. 2, 2001

(54) METHOD AND APPARATUS FOR DISTINGUISHING PARTICLES FROM SUBSURFACE DEFECTS ON A SUBSTRATE USING POLARIZED LIGHT

(75) Inventors: Yuri A. Eremin, Moscow (RU); John C. Stover; Craig A. Scheer, both of Charlotte, NC (US)

(73) Assignee: ADE Optical Systems, Charlotte, NC (US)

(*) Notice: Under 35 U.S.C. 154(b), the term of this patent shall be extended for 0 days.

(21) Appl. No.: 09/338,251

(22) Filed: Jun. 22, 1999

Related U.S. Application Data (60) Provisional application No. 60/090,323, filed on Jun. 23, 1998.

(51) Int. Cl.⁷ ................................................. G01N 21/00
(52) U.S. Cl. ................... 356/239.8; 356/369; 356/237.1
(58) Field of Search ................... 356/239.8, 369, 356/237.1, 239.1, 239.2, 239.7, 364–370

(56) References Cited

U.S. PATENT DOCUMENTS

| | | |
|---|---|---|
| 3,904,293 | 9/1975 | Gee . |
| 4,469,442 | 9/1984 | Reich . |
| 4,740,708 | 4/1988 | Batchelder . |
| 4,794,264 | 12/1988 | Quackenbos et al. . |
| 4,794,265 | 12/1988 | Quackenbos et al. . |
| 4,889,998 | 12/1989 | Hayano et al. . |
| 4,893,932 | 1/1990 | Knollenberg . |
| 4,933,567 | 6/1990 | Silva et al. . |
| 4,966,457 | 10/1990 | Hayano et al. . |
| 5,355,212 | 10/1994 | Wells et al. . |
| 5,389,794 | 2/1995 | Allen et al. . |
| 5,424,536 | 6/1995 | Moriya . |
| 5,465,145 | 11/1995 | Nashashige et al. . |
| 5,486,919 | 1/1996 | Tsuji et al. . |
| 5,625,193 | 4/1997 | Broude et al. . |
| 5,712,701 | 1/1998 | Clementi et al. . |
| 5,936,726 | * 8/1999 | Takeda et al. ................... 356/237.2 |
| 6,034,776 | * 3/2000 | Germer et al. ................... 356/369 |

FOREIGN PATENT DOCUMENTS

| | | |
|---|---|---|
| 5-142156 | 6/1993 | (JP) . |
| 06229939 | 8/1994 | (JP) . |

\* cited by examiner

Primary Examiner—Frank G. Font
Assistant Examiner—Layla Lauchman
(74) Attorney, Agent, or Firm—Alston & Bird LLP (57) ABSTRACT

Particles are distinguished from pits, voids, scratches, and other subsurface defects in a surface of a substrate by impinging the defect with polarized light and integrating light scattered by the defect over a wide angular range to produce a total integrated response. Using a P-polarized incident light beam, particles are distinguished from subsurface defects by comparing the total integrated responses, which vary with changes in the incident angle. Alternatively, the defect is impinged with a P-polarized incident beam at a defined incident angle, and is then impinged with an S-polarized beam at the same incident angle. Total integrated responses are measured for both beams and a P-to-S ratio of the responses is calculated. Particles are distinguished from subsurface defects by comparing the P-to-S ratio to a predetermined threshold value which separates particles from subsurface defects.

20 Claims, 7 Drawing Sheets

METHOD AND APPARATUS FOR DISTINGUISHING PARTICLES FROM SUBSURFACE DEFECTS ON A SUBSTRATE USING POLARIZED LIGHT

CROSS-REFERENCE TO RELATED APPLICATION

This application claims the benefit of U.S. Provisional Application Ser. No. 60/090,323 filed Jun. 23, 1998.

FIELD OF THE INVENTION

The present invention relates to methods and apparatus for performing optical inspection of smooth manufactured surfaces of a substrate such as silicon wafers, magnetic media, glass plates, or the like, so as to detect defects including particles on the surface and subsurface defects such as pits and scratches in the surface and voids below the surface. More particularly, the invention relates to methods and apparatus for discriminating between particles and subsurface defects.

BACKGROUND OF THE INVENTION

Optical inspection techniques are increasingly being used for inspecting smooth surfaces of articles such as silicon wafers, computer disks, glass plates, and the like, for detecting very small defects. In many applications, it is desirable to be able to detect particles on the surface, pits in the surface, voids beneath the surface, microscopic scratches, and other types of defects.

Optical inspection methods based on the scattering of light from a defect have been developed and have been used for several years as a means of detecting and mapping defects and contamination on smooth surfaces. Most such methods have not been capable of discriminating between particles and subsurface defects, but merely detect the presence of a defect and its size.

In some applications, however, it can be important to be able to distinguish particles from subsurface defects. For example, in the semiconductor industry, silicon wafers that are found to have particles on the surface after polishing can be subjected to further cleaning operations in order to cure the defects. However, if the defects are pits in the surface or voids beneath the surface, further cleaning will not be effective for curing the defects. If the wafer inspection system is not capable of discriminating between the two types of defects, then inevitably time and resources will be futilely expended attempting to remedy some defective wafers having pits and/or voids. Furthermore, if the manufacturer is unable to classify defects as pits or voids, it is more difficult to take appropriate steps to reduce the incidence of pits and voids, which typically are caused during the bulk manufacturing of silicon from which wafers are made.

Similarly, patterned wafers are typically inspected following a chemical-mechanical polish (CMP) operation in order to detect surface defects in the polished surface of the patterned wafer. In the course of the CMP operation, microscopic scratches (e.g., on the order of 0.25 $\mu$m wide by 0.25 $\mu$m deep by 5 $\mu$m long) are sometimes formed in the oxide film layer of the wafer. This can be caused, for example, by contamination of a polishing pad by foreign matter. It is important to be able to distinguish between such scratches and particles on the surface of the wafer. If the defect can be identified as a scratch, then adjustments can be made to the CMP process in order to prevent or reduce the scratching.

Accordingly, recent efforts in the optical inspection field have focused on discriminating between particles and subsurface defects such as pits, scratches, and voids. For example, commonly owned U.S. Pat. application Ser. No. 08/958,230 filed Oct. 27, 1997, hereby incorporated herein by reference, discloses methods and apparatus for distinguishing between pits and particles by detecting variations in the intensity of scattered light with angular position relative to the defect.

SUMMARY OF THE INVENTION

The present invention enables discrimination of particles and subsurface defects by detecting changes in the total intensity of light scattered over a wide angular range as a function of the incident angle of a polarized light beam, or as a function of the polarization of the incident beam.

In accordance with a preferred embodiment of the invention, a method of differentiating particles and subsurface defects comprises directing a first beam of P-polarized light to impinge at a first incident angle on the surface being inspected, collecting light scattered from the surface over a predetermined area, and integrating the intensities of the scattered light over this area to form a first integrated response. A second beam of the P-polarized light is directed to impinge on the surface at a second incident angle which is greater than the first incident angle, and light scattered from the surface is collected and the intensities of the scattered light are integrated over the same area to form a second integrated response. The first and second integrated responses are compared to determine whether a defect is a particle or a subsurface defect. Particles are characterized by the second integrated response being greater than the first integrated response, while subsurface defects are characterized by the second integrated response being less than the first integrated response.

In a preferred embodiment of the invention, the first beam is directed at an incident angle of about 5–20 degrees (measured from the surface normal) and the second beam is directed at an incident angle of about 50–75 degrees. The scattered light advantageously is collected over a range of angles from negative to positive as measured from a plane normal to the surface.

Various devices may be used for collecting the scattered light and integrating the intensities to produce the integrated responses. In one preferred embodiment, a wide angle collector is used to collect the scattered light. In another preferred embodiment, a plurality of collectors are distributed over the angular range for collecting the scattered light.

In accordance with another preferred embodiment of the invention, particles are distinguished from subsurface defects on the basis of the ratio of the integrated response produced by a P-polarized incident beam to the integrated response produced by an S-polarized incident beam at the same incident angle. More specifically, the defect is a particle if the ratio of P-to-S integrated response is greater than a predetermined value; conversely, if the P-to-S ratio of integrated response is less than the predetermined value, then the defect is a subsurface defect such as a pit, scratch, or void. Defects can be classified as particles based on these ratios regardless of the composition of the particles or their shapes.

In still another embodiment of the invention, an incident beam containing both P-polarized and S-polarized light can be used, such as circularly or elliptically polarized light. Two collectors are disposed symmetrically on either side of the incident plane. One of the collectors detects P-polarized light components of the scattered light, and the other collector detects S-polarized light components of the scattered light. The P-to-S ratio is then used to classify defects as pits or particles.

BRIEF DESCRIPTION OF THE DRAWINGS

The above and other objects, features, and advantages of the invention will be me more apparent from the following description of certain preferred embodiments thereof, when taken in conjunction with the accompanying drawings in which.

DETAILED DESCRIPTION OF THE DRAWINGS

The invention is now explained by reference to certain preferred embodiments thereof. It is to be understood, however, that the invention is not limited to the described and illustrated embodiments.

Figure 1:
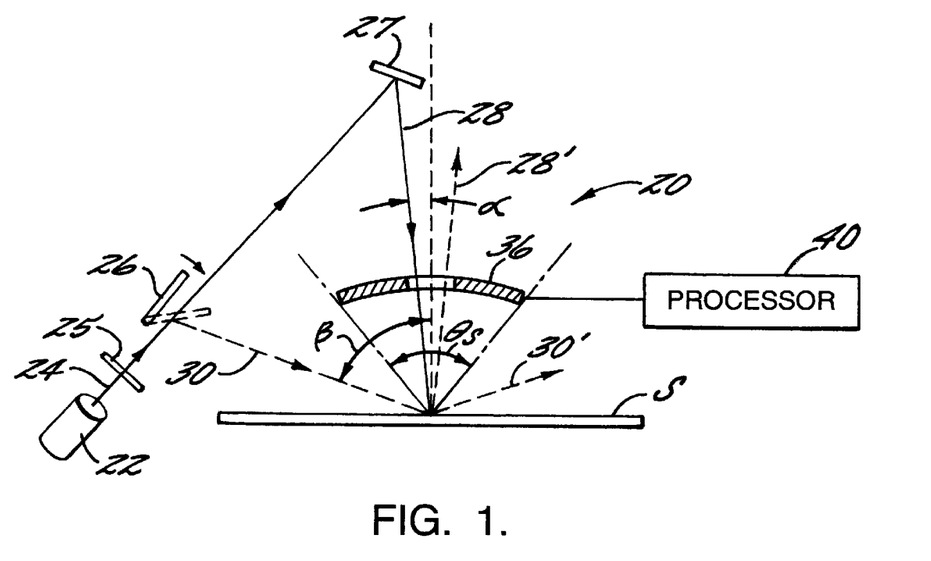
FIG. 1 is a schematic side elevational view of an apparatus in accordance with one embodiment of the invention for discriminating between particles and subsurface defects.

With reference to FIG. 1, an apparatus in accordance with one preferred embodiment of the invention for detecting particles and subsurface defects on a surface of a substrate is broadly designated by reference numeral 20. The apparatus 20 includes a light source 22 operable for producing a beam 24 of light. Preferably, the light source 22 comprises a laser which produces light in the visible spectrum. The apparatus 20 also includes a beam polarizer 25 for P-polarizing the source beam 24. The apparatus 20 further includes suitable optics such as the mirrors 26 and 27 depicted in FIG. 1, which are operable to selectively direct the beam 24 as a first beam 28 of P-polarized light so as to impinge on a given location on the surface S at a first incident angle α, or as a second beam 30 of P-polarized light so as to impinge on the same location on the surface S at a second incident angle β which is greater than the first angle α. It will of course be appreciated that instead of using a single light source 22 and optical guides 26 and 27 for creating the two incident beams 28 and 30, alternatively a pair of light sources could be appropriately positioned for directing beams at the desired incident angles. The specularly reflected light 28' and 30' respectively corresponding to the incident beams 28 and 30 can be collected, if desired, by suitable collectors (not shown). However, the present invention is mainly concerned with the light scattered by defects on or in the surface S, and this scattered light can be distributed over a wide angular range.

The apparatus 20 includes a collector 36 operable for collecting light scattered from the surface S over a wide angular range $\theta_s$ and detecting the intensity of the scattered light that is collected. The collector 36 may be any suitable device or combination of devices capable of collecting the scattered light and measuring the intensity of the collected light; for example, a wide-angle lens or a plurality of lenses and/or mirrors may be used for collecting and focusing the scattered light onto one or more detectors. By collecting light scattered over the angular range $\theta_s$ detecting its intensity, the collector 36 effectively integrates the scattered light distribution. Accordingly, the collector 36 detects a scattered light intensity referred to herein as the total integrated response (TIR).

A processor 40 connected to the collector 36 compares the TIR values corresponding to the incident beams 28 and 30 and based on the comparison determines whether a defect is a particle or a subsurface defect. The invention relies on the discovery that the TIR produced by a particle on the surface S increases with increasing incident angle of a P-polarized light beam. Conversely, the TIR produced by a subsurface defect, such as a pit, scratch, or void, decreases with increasing incident angle. Thus, this difference in response characteristic can be used to distinguish between particles and subsurface defects.

FIGS. 3–12 illustrate the effects on TIR of various defect sizes, shapes, and particle material types for both P-polarized and S-polarized incident beams, as a function of the incident angle. The data plotted in FIGS. 3–12 were derived from mathematical models based on a technique known as the discrete sources method (DSM), which has been verified experimentally in the published literature. Over a wide range of particle sizes, materials, and shapes, the model consistently predicts an increase in TIR with increasing incident angle. Conversely, over a wide range of pit sizes and subsurface void sizes, the model consistently predicts a decrease in TIR with increasing incident angle.

This effect has been confirmed experimentally for a limited number of defect types. Specifically, scatter was measured from 100 nm-diameter polystyrene latex (PSL) spheres on a silicon substrate using a 488 nm-wavelength laser light source producing beams of P-polarized light at incident angles of 0° and 70°. Scattered light was collected using a collection aperture of 42° wide centered with respect to the plane of incidence at 35° from the surface normal. The ratio of the TIR measured at 70° incident angle to the TIR measured at 0° incident angle (hereinafter referred to as $P_{70}/P_0$) was 2.11, versus 1.82 predicted by the mathematical model.

A further experiment was performed with the above-described test setup to assess the effects on TIR from manufactured pits in the surface of a silicon substrate. Although there is some uncertainty in the magnitude of the TIR measurements taken, due to various factors such as lack of precise control over the exact shapes of the pits and the fact that light was scattered from several pits simultaneously, nevertheless the measured $P_{70}/P_0$ ratio was 0.94, indicating a decrease of TIR with increasing incident angle. Thus, the model predictions are borne out by the experimental results.

Figure 3:
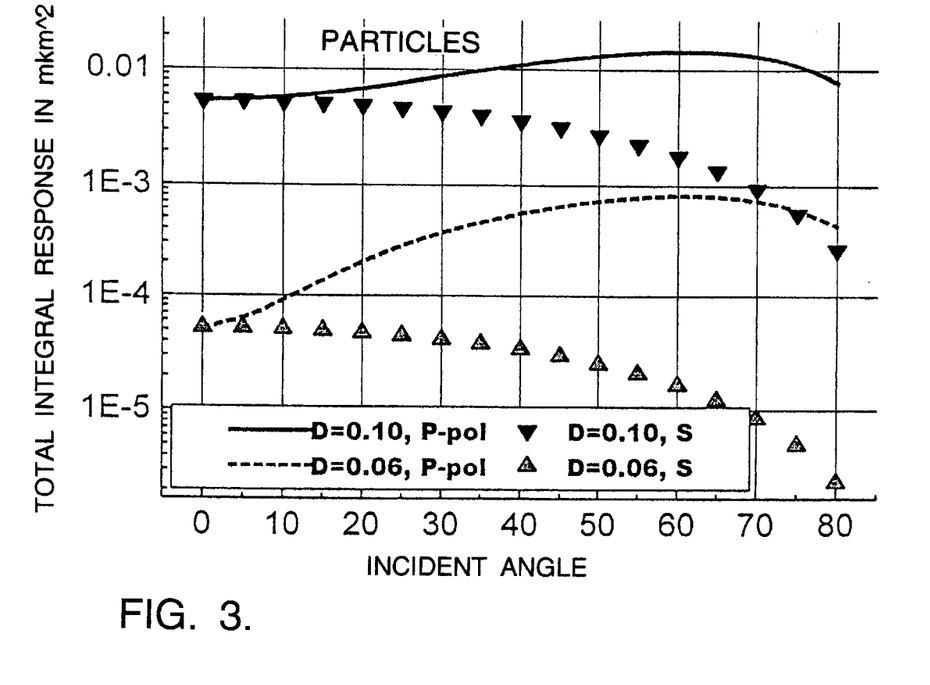
FIG. 3 shows a graph on which are plotted mathematical model predictions of total integrated responses (TIR) produced by small spheres of polystyrene latex (PSL) on the surface of a silicon substrate, for both P-polarized and S-polarized incident light beams, as functions of the incident angle.

FIGS. 3–12 show the results of applying the model to assess the effects that various defect and substrate parameters have on the TIR-incident angle relationship. FIG. 3 shows a graph on which are plotted mathematical model predictions of TIR produced by 100 nm-diameter and 60 nm-diameter spheres of PSL on the surface of a silicon substrate, for both P-polarized and S-polarized incident light beams, as functions of the incident angle. The model indicates that for a P-polarized incident beam, TIR increases with increasing incident angle. However, with an S-polarized incident beam, TIR decreases with increasing incident angle. The effect is consistent for both the 100 nm and 60 nm PSL spheres.

Figure 4:
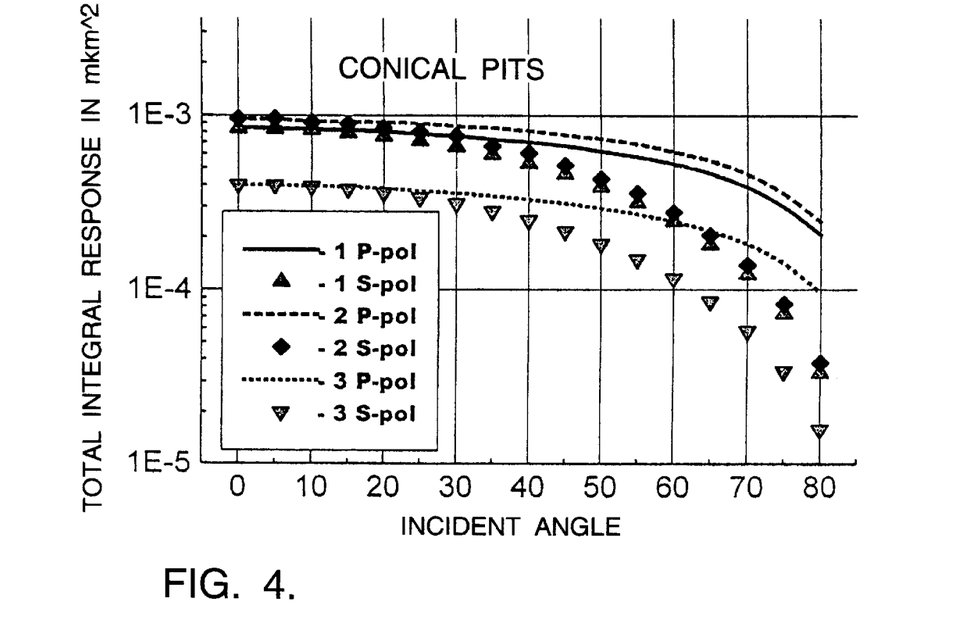
FIG. 4 shows a graph similar to FIG. 3, but showing the predicted TIR produced by small pits in the substrate surface.

FIG. 4 shows a graph similar to FIG. 3, but depicting the predicted TIR produced by a conical pit having a 60° included angle formed in the surface of a silicon substrate, a truncated conical pit 60 nm deep, and a 90° conical pit. For both P-polarized and S-polarized light sources, TIR decreases with increasing incident angle. It will be noted by comparing FIGS. 3 and 4, however, that at a given incident angle, for example 70°, the ratio of TIR produced by P-polarized light to TIR produced by S-polarized light (hereinafter referred to as the P-to-S ratio) is larger for particles than it is for pits.

Figure 5:
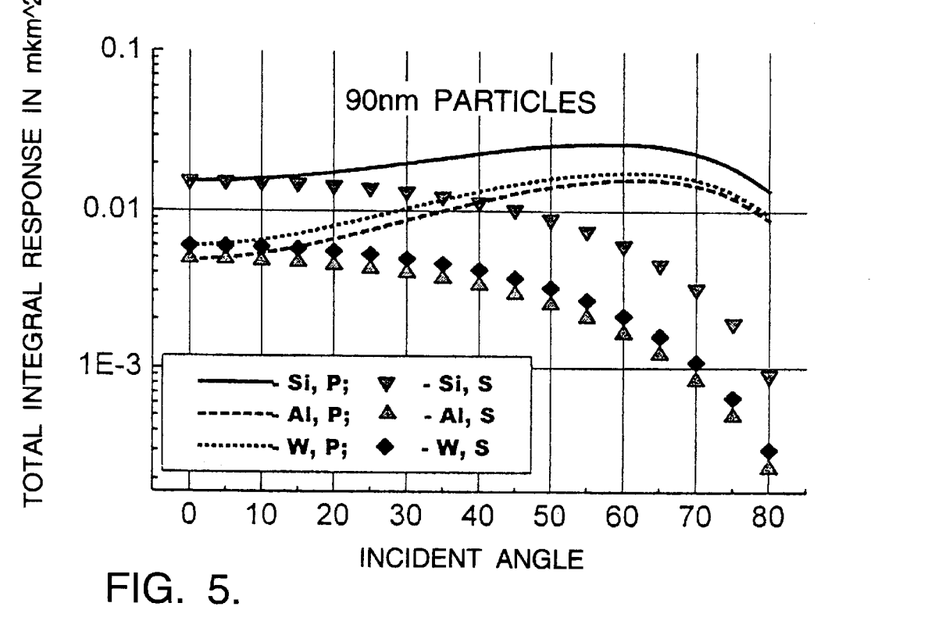
FIG. 5 shows a graph similar to FIGS. 3 and 4, comparing the predicted TIR produced by 90 nm-diameter spheres of silicon, aluminum, and tungsten.
Figure 6:
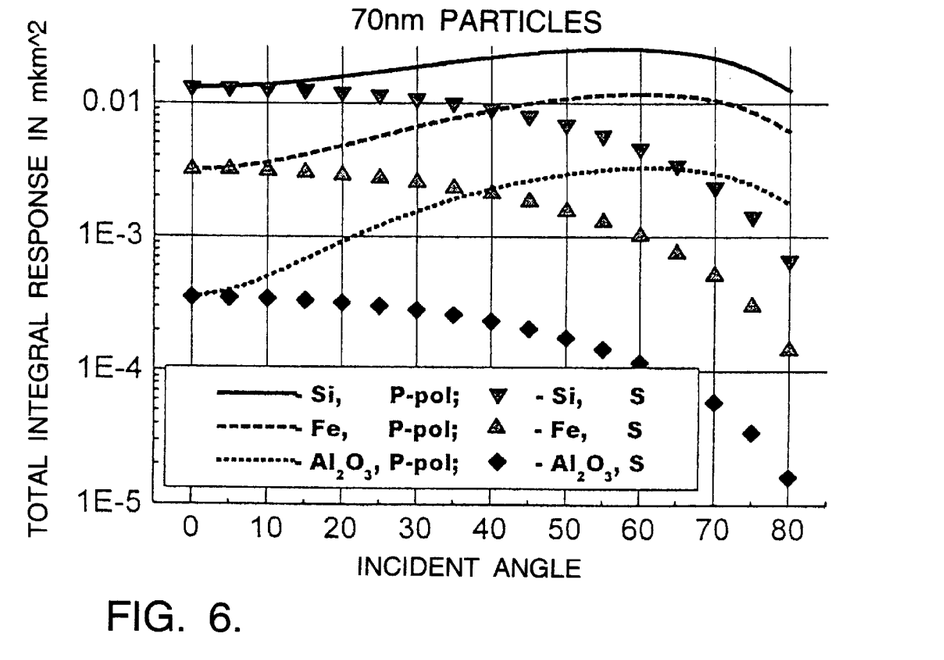
FIG. 6 shows a graph similar to FIG. 5, comparing the predicted TIR produced by 70 nm-diameter spheres of silicon, iron, and $Al_2O_3$.

FIGS. 5 and 6 show the model-predicted effects that the material type of a particle has on the TIR-incident angle relationship. FIG. 5 shows predicted TIR versus incident angle for 90 nm-diameter spherical particles of silicon, aluminum, and tungsten. For all of the particle types, TIR increases with increasing incident angle using P-polarized light and decreases with increasing incident angle using S-polarized light. FIG. 6 indicates that the model predicts similar results for 70 nm-diameter particles of silicon, iron, and $Al_2O_3$.

Figure 7:
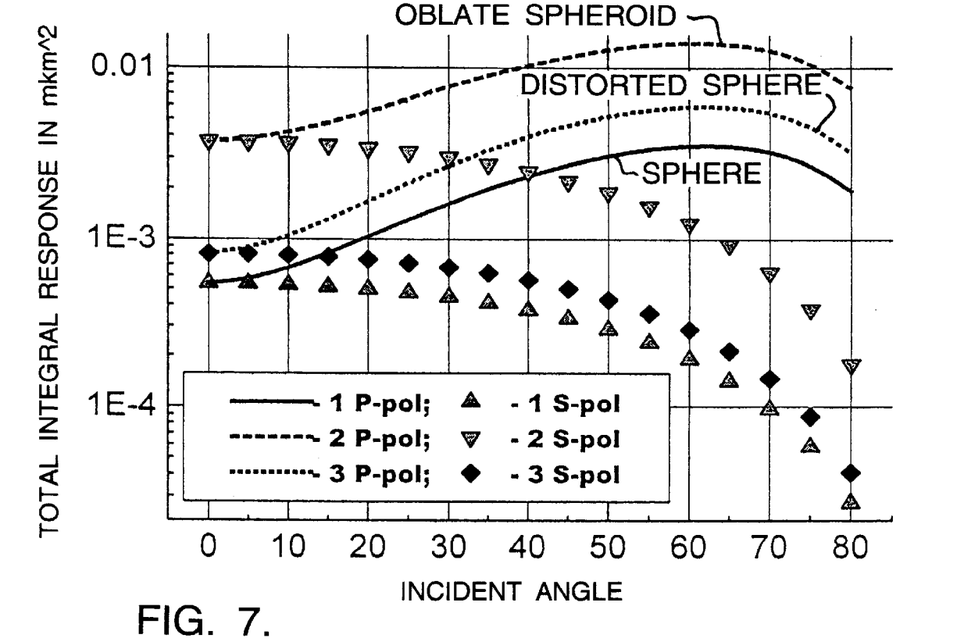
FIG. 7 shows a graph similar to FIG. 6, comparing the predicted TIR produced by $Al_2O_3$ particles of equal volume and various shapes.

FIG. 7 shows the model-predicted effects that particle shape has on the TIR-incident angle relationship. For spherical, oblate spheroidal, and distorted spherical particles of $Al_2O_3$ having equal volumes, the model indicates that TIR increases with increasing incident angle using P-polarized light and decreases with increasing incident angle using S-polarized light.

Figure 8:
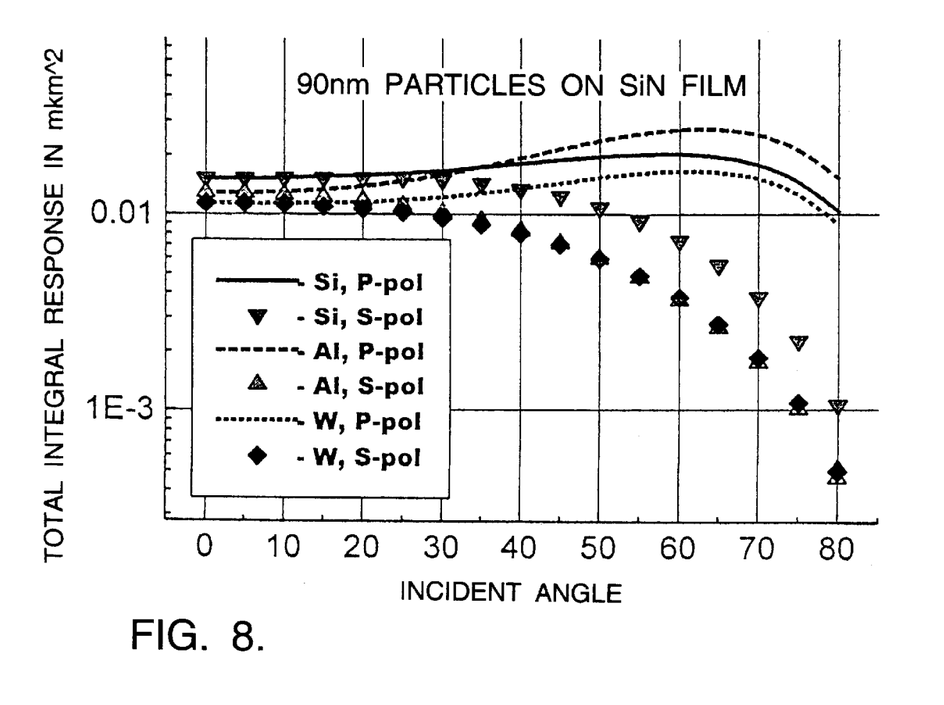
FIG. 8 shows a graph similar to FIG. 5, except that the particles are located on a 150 nm-thick SiN film deposited on the surface of the silicon substrate.
Figure 9:
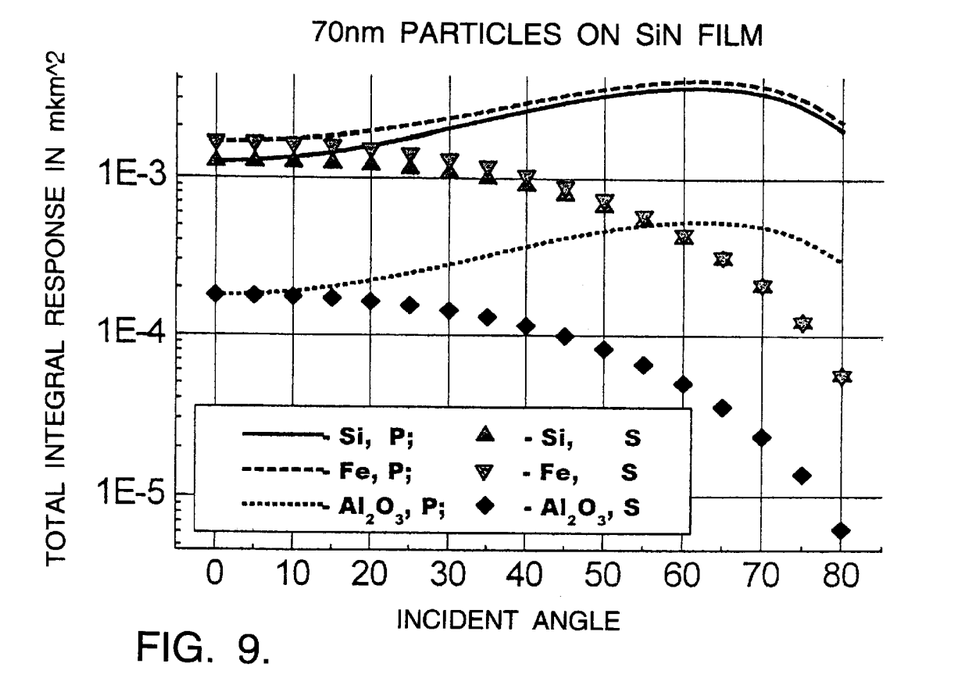
FIG. 9 shows a graph similar to FIG. 6, except that the particles are located on a 150 nm-thick SiN film deposited on the surface of the silicon substrate.

FIGS. 8 and 9 are analogous to FIGS. 5 and 6, except that the particles are disposed on a 150 nm-thick film of silicon nitride (SiN) that is deposited on a silicon substrate. FIGS. 8 and 9 confirm that the effect particles have on the TIR-incident angle relationship is qualitatively the same for a SiN film-covered silicon substrate as it is for a silicon substrate with no film.

Figure 10:
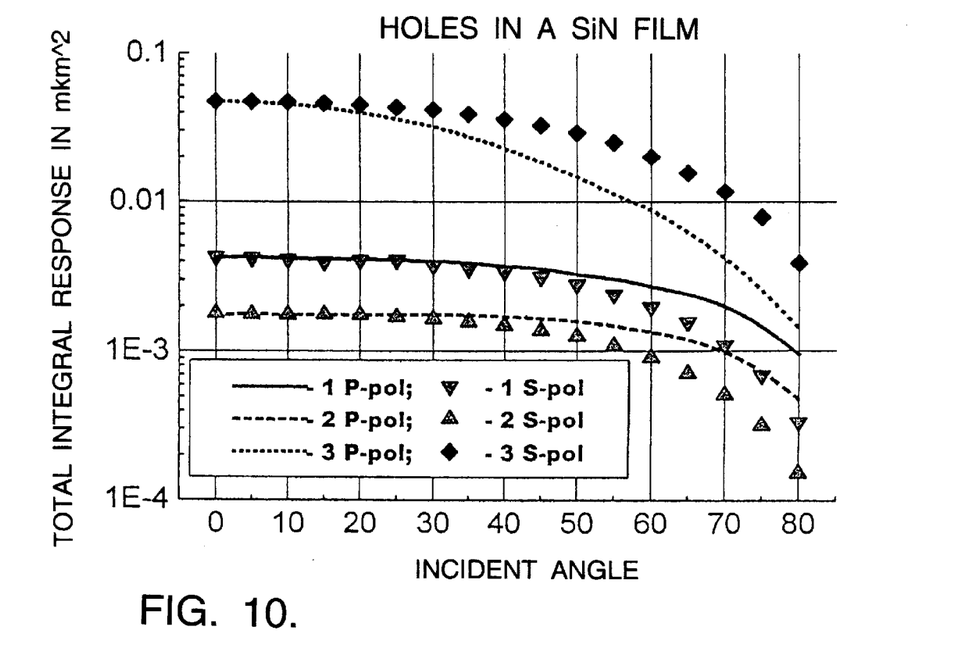
FIG. 10 shows a graph depicting the predicted TIR produced by pits of various sizes and shapes in a 120 nm-thick SiN film and in a 200 nm-thick film on a silicon substrate.
Figure 11:
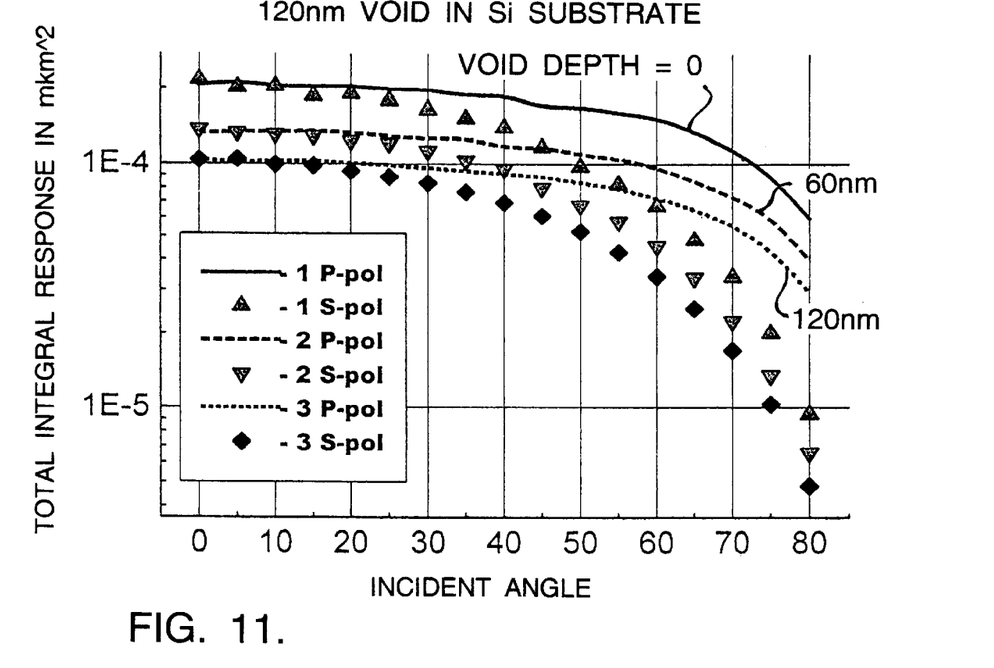
FIG. 11 shows a graph depicting the predicted TIR produced by 120 nm voids located at various depths below the surface of a silicon substrate.
Figure 12:
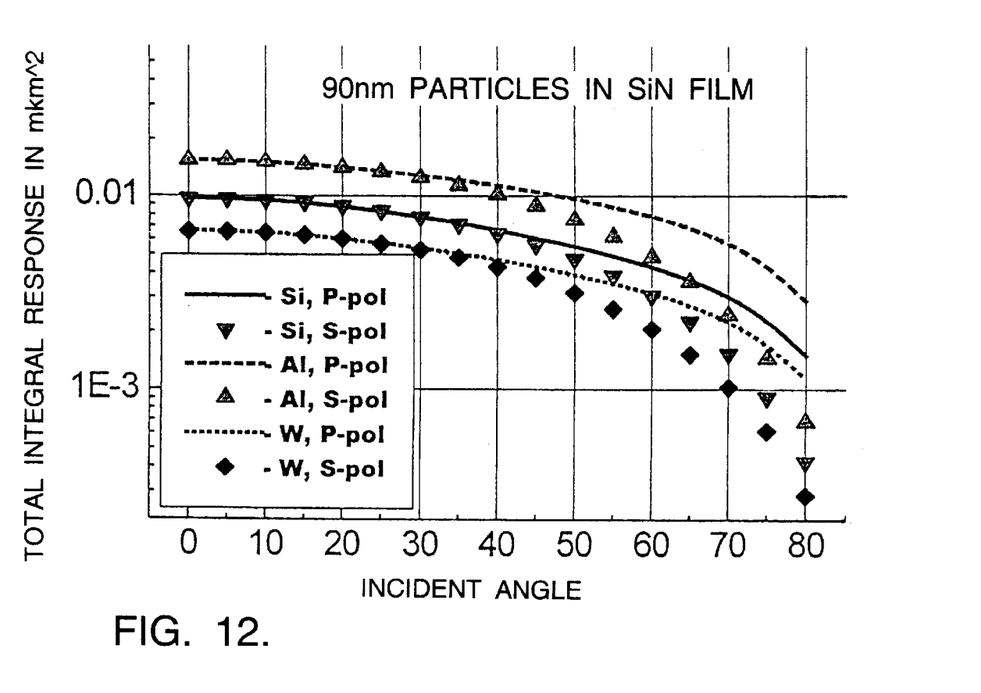
FIG. 12 shows a graph comparing the predicted TIR produced by 90 nm-diameter spheres of silicon, aluminum, and tungsten located inside a 150 nm-thick SiN film on a silicon substrate.

FIGS. 10–12 present model-predicted results for various subsurface defects including pits, voids, and particles located beneath the surface. FIG. 10 presents the model-predicted TIR versus incident angle for holes in a SiN film on a silicon substrate. Three different geometries were modeled: a 120 nm-diameter cylindrical hole in a 120 nm-thick SiN film; a truncated conical hole in a 120 nm-thick SiN film, the diameter of the hole at the surface being 120 nm and the diameter of the hole at the base being 60 nm; and a 200 nm-diameter cylindrical hole in a 200 nm-thick SiN film. For all three geometries, TIR decreases with increasing incident angle for both P-polarized and S-polarized light. It will also be noted by comparing FIGS. 9 and 10 that the P-to-S ratio at a given incident angle, for example 70°, is smaller for the holes in the SiN film than for the particles on the SiN film.

FIG. 11 shows the model-predicted TIR for a 120 nm void at various depths below the surface of a silicon substrate. The results are qualitatively similar to the results for the holes as shown in FIG. 10. Finally, FIG. 12 shows the model-predicted TIR for 90 nm-diameter spheres of silicon, aluminum, and tungsten located inside a 150 nm-thick SiN film. As for the other subsurface defects, TIR decreases with increasing incident angle for both P-polarized and S-polarized light.

Based on the information in FIGS. 3–12, it will be appreciated that particles are distinguishable from subsurface defects such as pits, voids, and subsurface particles, in terms of the trend of TIR with increasing incident angle of a P-polarized light beam. It will also be noted that particles are distinguishable from subsurface defects in terms of the P-to-S ratio of TIR at a given incident angle, the P-to-S ratio being relatively larger for particles than for subsurface defects.

Accordingly, a first method for discriminating between particles and subsurface defects in accordance with the invention is shown in FIG. 1. The method is based on impinging a region of a surface being inspected with a beam of P-polarized light at a first incident angle α, collecting light scattered from the surface over a wide angular range, and integrating the scattered light intensity to produce a first integrated response $R_1$. The region of the surface is also impinged with a second beam of the P-polarized light at a second incident angle β greater than the first angle α, the scattered light is collected over the same angular range, and the light intensity is integrated to produce a second integrated response $R_2$. The first and second integrated responses are compared to determine whether a defect is a particle or a subsurface defect. If $R_1$ is less than $R_2$, then the defect is a particle; otherwise, the defect is a subsurface defect.

Advantageously, the first incident angle α is about 5–20 degrees and the second incident angle β is about 50–75 degrees. However, other incident angles may be used if desired. In some applications, it may be desirable to use more than two incident beams, for example three incident beams at three different incident angles. The incident beams may be coplanar or in different planes. The center of the collector 36 may be located on a line normal to the surface S passing through the region impinged by the incident beams, or alternatively the center of the collector may be angularly offset from the surface normal.

Figure 2:
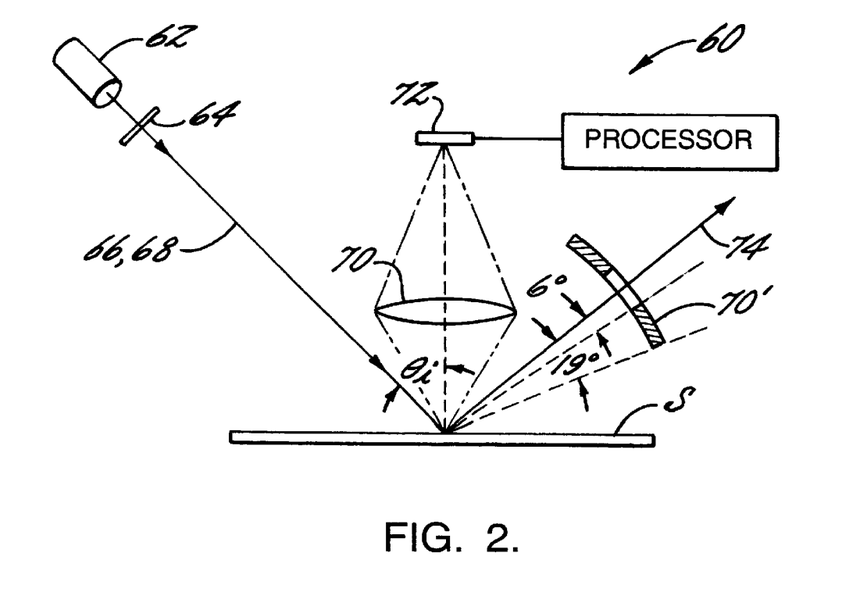
FIG. 2 is a view similar to FIG. 1, showing an alternative embodiment of an apparatus in accordance with the invention.

The invention also encompasses a second method and apparatus for distinguishing particles from subsurface defects, which is based on the phenomenon, noted above, that the P-to-S ratio of TIR at a given incident angle is greater for particles than for subsurface defects. FIG. 2 shows an apparatus 60 suitable for practicing the second method. The apparatus 60 includes a light source 62 operable to produce a light beam 63 and a polarizer 64 which is operable to selectively polarize the beam 63 from the light source 62 to produce either a P-polarized beam 66 or an S-polarized beam 68. For example, the polarizer 64 may be rotated about its axis in order to change the polarization of the output beam from P-polarization to S-polarization. The light source 62 and polarizer 64 are arranged to direct an incident beam 66, 68 to impinge on the surface S at an incident angle $\theta_i$. The apparatus 60 further includes a collector 70 for collecting scattered light over a wide angular range, and a detector 72 upon which the collector 70 focuses the collected light and which detects the intensity of the collected light.

In operation, the light source 62 is used to create a beam 63 and the polarizer 64 is positioned to produce a beam 66 of P-polarized light and direct the beam 66 onto the surface S. The collector 70 collects (i.e., integrates) the scattered light over the wide angular range and focuses the light on the detector 72, and the detector 72 produces a first integrated response. The light source 62 next is used to create a beam 63 and the polarizer is positioned to produce a beam 68 of S-polarized light and direct the beam 68 onto the surface S at the same point as the P-polarized beam 66. The collector 70 collects and focuses the scattered light onto the detector 72 which produces a second integrated response. The first and second integrated responses are compared to determine whether a defect is a particle or a subsurface defect. If the P-to-S ratio of the first to the second integrated response is greater than a predetermined value, then the defect is a particle. If the P-to-S ratio is less than the predetermined value, then the defect is a subsurface defect.

It will be understood that although the apparatus 60 is illustrated as employing a single lens as the collector 70, various types of collectors can be used instead, including multiple lenses, one or more mirrors, or combinations of lenses and mirrors. For example, as shown in FIG. 2, instead of the collector 70 which is centered relative to the impingement point on the surface S, a forward collector 70' may be used which allows the specularly reflected beam 74 to pass through and which collects scattered light over a range of angles (e.g., about 6° to 19°) about the specularly reflected beam. Additionally, more than one detector can be used for measuring scattered light intensity at multiple locations, and the several individually measured intensities can be integrated to produce a total integrated response. Thus, the invention is not limited to any particular collector configuration.

Figure 13:
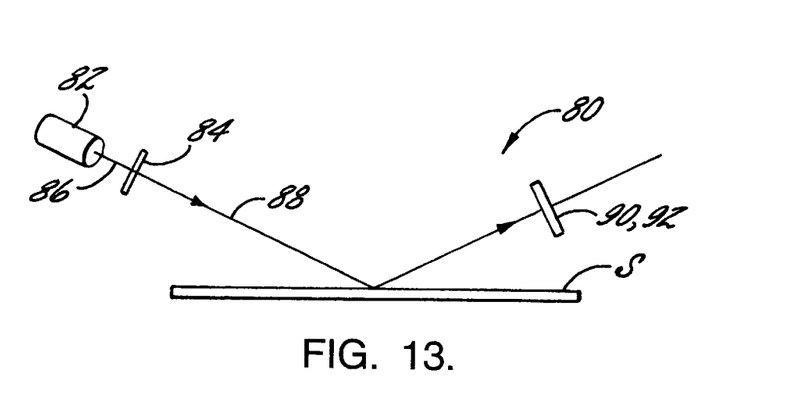
FIG. 13 is a side elevation of another preferred embodiment of an apparatus in accordance with the invention.
Figure 14:
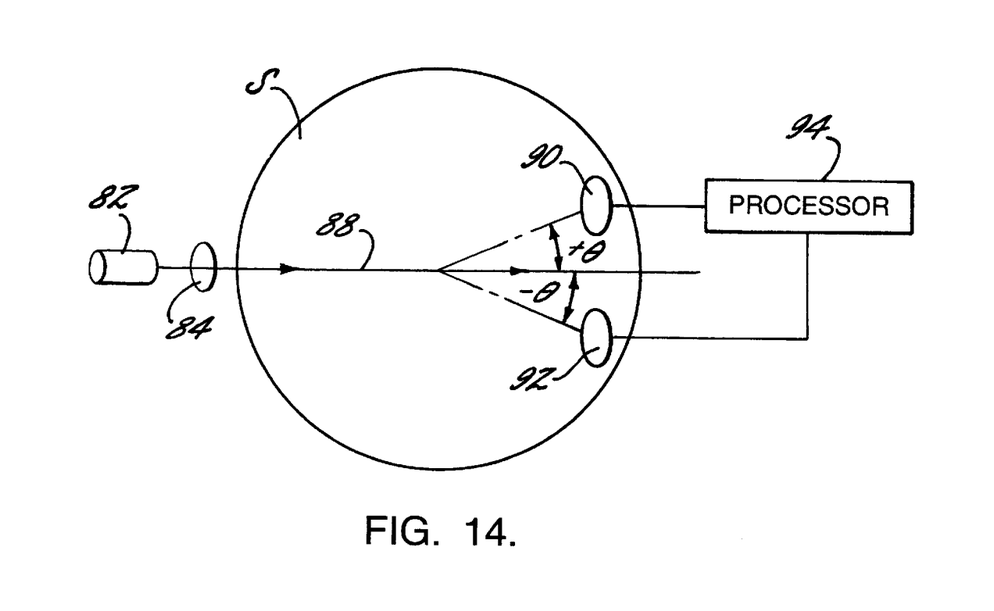
FIG. 14 is a top elevation of the apparatus of FIG. 13.

FIGS. 13 and 14 depict an apparatus 80 in accordance with yet another preferred embodiment of the invention. The apparatus 80 includes a light source 82 and a 45° polarizer 84 which operates upon the light beam 86 emitted by the light source 82 to produce an incident beam 88 which is 45° polarized. A pair of collectors 90 and 92 are positioned in a forward-scatter region relative to the location at which the incident beam 88 impinges the surface S. The collectors 90 and 92 are respectively located at $+\phi$ and $-\phi$ azimuth angles relative to the plane of incidence (i.e., the plane which is normal to the surface S and contains the incident beam 88). One of the collectors detects a P-polarized component of the scattered light received by the collector and provides a signal indicative of the intensity of the P-polarized component, and the other collector detects an S-polarized component of the scattered light received by the collector and provides a signal indicative of the intensity of the S-polarized component. A processor 94 receives the signals from the collectors 90, 92 and is operable to compare the relative intensities of the P-polarized and S-polarized components and to determine whether a defect is a particle or a subsurface defect based on the comparison. Thus, the apparatus 80 is advantageous in that only a single source polarization and a single incident angle are required. Although the collectors 90 and 92 are shown as being physically separate, they can instead be configured as separate portions of a single collector device disposed symmetrically about the incident plane.

Based on the foregoing description of certain preferred embodiments of the invention, persons of ordinary skill in the art will readily comprehend various modifications and substitutions of equivalents that can be made to the described embodiments. Such modifications and substitutions are intended to be encompassed within the scope of the invention as set forth in the appended claims.

What is claimed is:

1. A method for detecting a defect at a region on a surface of a substrate and for discriminating between particle defects and subsurface defects, the method comprising:

directing a first beam of P-polarized light to impinge at said region on the surface at a first incident angle;

collecting scattered light caused by the first beam over a predetermined area and integrating the intensities of the scattered light over said area to form a first integrated response;

directing a second beam of the P-polarized light to impinge at said region on the surface at a second incident angle which is greater than the first incident angle;

collecting scattered light caused by the second beam over said area and integrating the intensities of the scattered light over said area to form a second integrated response; and comparing the first and second integrated responses to determine whether a defect is a particle or a subsurface defect.

2. The method of claim 1, wherein the first beam is directed at an incident angle of about 5–20 degrees and the second beam is directed at an incident angle of about 50–75 degrees relative to a normal to the surface.

3. The method of claim 1, wherein the scattered light is collected over a range of angles from negative to positive relative to a plane normal to the surface.

4. The method of claim 1, wherein the steps of collecting the scattered light comprise using a wide angle collector to collect the light.

5. The method of claim 1, wherein the steps of collecting the scattered light comprise using a plurality of collectors to collect the light.

6. The method of claim 1, wherein the steps of collecting the scattered light and integrating the scattered light intensities comprise capturing the scattered light over the predetermined area and focusing the captured light onto a detector operable for measuring light intensity.

7. A method for detecting a defect at a region on a surface of a substrate and for discriminating between particle defects and subsurface defects, the method comprising:

directing a beam of P-polarized light to impinge at said region on the surface at a predetermined incident angle;

collecting scattered light caused by the P-polarized beam at a plurality of locations over a wide angular range and integrating the intensities of the scattered light from said locations to form a first integrated response;

directing a beam of S-polarized light to impinge at said region on the surface at the predetermined incident angle;

collecting scattered light caused by the S-polarized beam at said locations and integrating the intensities of the scattered light from said locations to form a second integrated response; and comparing the first and second integrated responses to determine whether a defect is a particle or a subsurface defect.

8. The method of claim 7, wherein the scattered light is collected over a range of angles from negative to positive relative to a plane normal to the surface.

9. The method of claim 7, wherein the steps of collecting the scattered light comprise using a wide angle collector to collect the light.

10. The method of claim 7, wherein the steps of collecting the scattered light comprise using a plurality of collectors distributed over the angular range to collect the light.

11. The method of claim 7, wherein the steps of collecting the scattered light and integrating the scattered light intensities comprise capturing the scattered light over the wide angular range and focusing the captured light onto a detector operable for measuring light intensity.

12. An apparatus for detecting a defect at a region on a surface of a substrate and for discriminating between particle defects and subsurface defects, the apparatus comprising:

at least one light source operable to create a first beam of P-polarized light and direct the first beam onto the region of the substrate surface at a first incident angle, and operable to create a second beam of P-polarized light and direct the second beam onto the region of the substrate surface at a second incident angle greater than the first incident angle;

a collection system positioned above the substrate surface for receiving light scattered from the surface to a plurality of locations distributed over a range of angles above the substrate surface, the collection system being operable for integrating intensities of the scattered light over said plurality of locations to produce total integrated response signals corresponding to the first and second P-polarized light beams; and a processor in communication with the collection system and operable for comparing the total integrated response signal caused by the first P-polarized light beam with the total integrated response signal caused by the second P-polarized light beam to determine whether a defect is a particle or a subsurface defect.

13. The apparatus of claim 12, wherein the collection system includes at least one wide angle collector.

14. An apparatus for detecting a defect at a region on a surface of a substrate and for discriminating between particle defects and subsurface defects, the apparatus comprising:

a light source operable to create a beam of P-polarized light and direct the P-polarized light beam onto the region of the substrate surface at a predetermined incident angle;

a light source operable to create a beam of S-polarized light and direct the S-polarized light beam onto the region of the substrate surface at the predetermined incident angle;

a collection system positioned above the substrate surface for receiving light scattered from the surface to a plurality of locations distributed over a range of angles above the substrate surface, the collection system being operable for integrating intensities of the scattered light over said plurality of locations to produce total integrated response signals corresponding to the P-polarized and S-polarized light beams; and a processor in communication with the collection system and operable for comparing the total integrated response signal caused by the P-polarized light beam with the total integrated response signal caused by the S-polarized light beam to determine whether a defect is a particle or a subsurface defect.

15. The apparatus of claim 14, wherein the collection system comprises at least one detector and at least one lens for collecting scattered light from said plurality of locations and focusing the scattered light onto said at least one detector.

16. The apparatus of claim 14, wherein the collection system includes at least one wide angle collector.

17. The apparatus of claim 14, wherein the collection system includes a generally annular collector having a center aperture, the annular collector being positioned to allow a specularly reflected beam to pass through the center aperture and being configured to collect scattered light over a wide angular range about the specularly reflected beam.

18. The apparatus of claim 14, wherein the light sources comprise a laser which creates a beam of laser light, and a polarizer which receives the beam of laser light and is selectively positionable in a first position to produce a P-polarized light beam and in a second position to produce an S-polarized light beam.

19. An apparatus for detecting a defect at a region on a surface of a substrate and for discriminating between particle defects and subsurface defects, the apparatus comprising:

a light source operable to create a beam of light containing both P-polarized and S-polarized components and to direct the light beam onto the region of the substrate;

first and second collectors positioned above the surface symmetrically on opposite sides of a plane of incidence that is normal to the surface and contains the incident light beam, the first collector being operable to detect a P-polarized component of scattered light and provide a signal indicative of intensity of the P-polarized component, the second collector being operable to detect an S-polarized component of scattered light and provide a signal indicative of intensity of the S-polarized component; and a processor which receives the signals from the collectors and is operable to compare the signals and determine whether a defect on the surface is a particle or a subsurface defect based on the comparison of the signals.

20. The apparatus of claim 19, wherein the first and second collectors are located in a forward-scattered position relative to the region of the surface impinged by the incident light beam.

* * * * *